United States Patent
Heruth

(10) Patent No.: US 6,394,981 B2
(45) Date of Patent: *May 28, 2002

(54) METHOD AND APPARATUS FOR DRUG INFUSION

(75) Inventor: Kenneth T. Heruth, Maple Grove, MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/416,151

(22) Filed: Oct. 11, 1999

Related U.S. Application Data

(62) Division of application No. 08/641,362, filed on Apr. 30, 1996, now Pat. No. 5,976,109.

(51) Int. Cl.⁷ .................... A61M 5/145; A61M 5/155
(52) U.S. Cl. .................... 604/140; 604/143; 604/146; 604/150; 604/151; 604/891.1; 604/93; 604/141
(58) Field of Search .................... 604/131, 132, 604/141, 143, 149, 214, 218, 315, 316, 88, 93, 140, 146, 150–155, 891.1

(56) References Cited

U.S. PATENT DOCUMENTS

| | | | |
|---|---|---|---|
| 2,972,991 A | | 2/1961 | Burke |
| 3,572,979 A | * | 3/1971 | Morton .................. 417/427 |
| 3,966,358 A | * | 6/1976 | Heimes et al. .......... 417/12 |
| 4,265,241 A | * | 5/1981 | Portner et al. .......... 128/260 |
| 4,266,541 A | | 5/1981 | Landau |
| 4,351,335 A | * | 9/1982 | Whitney et al. ............ 128/218 |
| 4,457,752 A | * | 7/1984 | Vadasz ..................... 604/135 |
| 4,581,018 A | * | 4/1986 | Jassawalla et al. ........ 604/153 |
| 4,626,243 A | * | 12/1986 | Singh et al. ............... 604/141 |
| 5,041,094 A | * | 8/1991 | Perego et al. .............. 604/143 |
| 5,176,641 A | * | 1/1993 | Idriss ........................ 604/133 |
| 5,348,539 A | * | 9/1994 | Herskowitz ............... 604/141 |
| 5,399,166 A | * | 3/1995 | Laing ........................ 604/146 |
| 5,476,449 A | * | 12/1995 | Richmond ................. 604/87 |
| 5,514,103 A | * | 5/1996 | Srisathapat et al. ....... 604/141 |
| 5,700,245 A | * | 12/1997 | Sancoff et al ............ 604/145 |
| 5,707,361 A | * | 1/1998 | Slettenmark ............. 604/131 |
| 5,766,150 A | * | 6/1998 | Langkau ................... 604/93 |
| 5,785,688 A | * | 7/1998 | Joshi et al. ................ 604/141 |
| 5,830,187 A | * | 11/1998 | Kriesel et al. ............ 604/132 |
| 5,836,915 A | * | 11/1998 | Steinbach et al. ........ 604/131 |
| 5,848,991 A | * | 12/1998 | Gross et al. .............. 604/140 |
| 5,976,109 A | | 11/1999 | Heruth |
| 5,980,489 A | * | 11/1999 | Kriesel ..................... 604/131 |
| 6,007,518 A | * | 12/1999 | Kriesel et al. ............ 604/131 |
| 6,027,491 A | * | 2/2000 | Hiejima et al. .......... 604/891.1 |

FOREIGN PATENT DOCUMENTS

DE      40 39 191 C1     11/1991

* cited by examiner

Primary Examiner—Sharon Kennedy
(74) Attorney, Agent, or Firm—Thomas G. Berry; Eric R. Waldkoetter

(57) ABSTRACT

The present disclosure describes a system wherein a drug or other fluid to be delivered to a specific desired location within the body is stored in a reservoir that is directly displaced by a force to infuse the drug from the device into the patient. Several specific methods are used to displace the reservoir, including, generally, hydraulic displacement, mechanical screw-type displacement, and spring force displacement of the fluid reservoir.

10 Claims, 3 Drawing Sheets

METHOD AND APPARATUS FOR DRUG INFUSION

This is a divisional of application Ser. No. 08/641,362, filed Apr. 30, 1996, now U.S. Pat. No. 5,976,109, issued Nov. 2, 1999.

FIELD OF THE INVENTION

The present invention relates generally to a method and apparatus for the delivery of fluids to a desired location within the body; and more particularly, relates to an implantable drug infusion device for delivery of pharmaceutical agents or other fluids directly from a reservoir within the device to a specific desired location within a patient's body.

BACKGROUND OF THE INVENTION

Implantable drug infusion devices usually are implanted for several years, during which time there is no opportunity to service or repair these devices. Accordingly, both the implanted device and the drug to be infused must remain operative and be stable for a long period.

The current trend is toward extending significantly the intended life of implanted drug infusion devices. Further, new drugs having different physical and chemical properties are continually being developed, the use of which may not be sufficiently compatible or properly interactive with current devices.

Conventional implantable fluid delivery systems for drug infusion typically include a reservoir to store the fluid, and a separate pump or other flow control device to deliver the fluid. This type of implantable drug infusion system is shown generally in FIG. 1. Reservoirs in conventional implanted drug infusion devices undergo little motion, so that the materials which form the reservoir can be selected primarily for compatibility with the drug that is to be delivered. Pumps, on the other hand, typically have many moving parts. The materials from which the pumps are made thus must be selected for specific mechanical properties, such as flexibility, durability, and strength. The materials used may not exhibit all desirable mechanical properties, or may not be compatible with some drugs to be infused. An example is a silicone tube in a peristaltic pump. Silicone is very flexible and durable, but is permeable to many fluids and is not as strong as other elastomers.

With respect to another incongruity of design objectives, because implantable infusion devices preferably are small in size, the devices typically have only limited internal space, so that any materials used in the manufacture of the device must be of the type that can be used to manufacture very small parts. One example of such a material is silicon formed by micromachining. Silicon, however, is difficult to join to other materials.

Along the same lines, although it is desirable to have implantable fluid delivery systems that are small in size, the reduced size of certain conventional devices can be problematic in some applications. For example, pumps or valves with very small passages are not able to effectively deliver certain fluids. Some drugs, such as insulin, often are damaged by shear forces when flowing through such small passages.

Finally, another design incongruity arises with conventional drug infusion devices in which the drug is routed from the reservoir to the pump, and then to the device outlet where it is delivered to a desired location within the body. A certain amount of the drug thus is contained in the pump and fluid passages. This fluid, held in what commonly is referred to as the "dead space," must be displaced whenever the drug in the reservoir is changed. Delivery systems with relatively more dead space require more unused, unwanted drug to be infused before the drug can be changed.

SUMMARY OF THE INVENTION

The fluid delivery assembly and method of the present invention overcomes the above-noted and other shortcomings of prior drug infusion systems. In accordance with the present invention, a drug or other fluid to be delivered to a specific desired location within the body is stored in a reservoir that is directly displaced by a force to infuse the drug from the device into the patient. Several methods can be used to displace the reservoir, which are described in more detail below. For simplicity the present invention is described herein in terms of three presently preferred embodiments which include, generally, hydraulic displacement, mechanical screw-type displacement, and spring force displacement of the fluid reservoir. However, one of ordinary skill in the art having the benefit of this disclosure will recognize that the invention is not limited strictly to the embodiments described herein. The Figures and other description contained herein is merely illustrative of the present invention. Actual implementation of the present invention in an implantable drug infusion device will undoubtedly vary depending upon the particular circumstances involved with its intended use, particularly with respect to the exact shape, size, specifications, etc. of the device. In any event each embodiment herein described incorporates the teachings of the present invention, and achieves the advantages of (a) eliminating contact and interaction between the drug and, other materials, including those comprising the pump; (b) eliminating small drug passages, for example, through the pump; and (c) of allowing controlled filling and emptying of the drug reservoir.

The first preferred method of displacing the reservoir, given as an example, is hydraulic. See FIGS. 2 and 3. In this configuration, three separate reservoir compartments are used along with a separate pump. The pump does not contact the drug, but recirculates a working fluid inside the device. The working fluid can be selected to be non-corrosive, or even to enhance the operation of the pump. Again, the choice of working fluid depends upon the circumstances involved in a particular application. However, examples of working fluids include sterile water, sterile saline, silicone oil, or a lubricant.

In operation, the pump withdraws the working fluid from the bottom reservoir and pumps it into an intermediate reservoir under the drug reservoir. The drug and intermediate reservoirs are separated by, for example, a diaphragm (See FIG. 2) or a piston (See FIG. 3). Of particular importance is that the drug and intermediate reservoirs be sealed, so that no fluid may pass from one into the other.

As the intermediate reservoir fills, and the drug reservoir is displaced, the drug is forced out of the device. The pump is programmable to any pattern or rate utilized in an implantable device. The drug infusion will follow the rate or pattern programmed. Examples of program rates and patterns include those commonly used with the SynchroMed™ Programmable Pump, available commercially from Medtronic, Inc., Minneapolis, Minn.

A means of maintaining constant pressure in the device, such as a volatile fluid, is required under the internal drug reservoir. To refill the drug reservoir, a syringe is introduced into the reservoir via a hypodermic needle. The drug exit path is closed and the pump is then reversed to draw the drug from the syringe into the reservoir. This method also eliminates the possibility of forcing the drug into the reservoir with the syringe and damaging the device or over-infusing the drug.

In the second preferred embodiment, the internal drug reservoir is directly displaced mechanically, either by a motor and lead screw (See FIG. 4) or a motor and worm gear (See FIG. 5).

In the first configuration of the second preferred embodiment, the motor rotates and displaces a nut on the lead screw. The nut is attached directly to the reservoir base and directly displaces it as it moves. This system is less susceptible to changes in pressure inside the device during operation. However, a volatile fluid still may be used to ensure that a relatively constant internal pressure is maintained. Again, the motor may be programmed to any pattern or rate, such as those used in commercially available implantable devices like the SynchroMed™, and the motor is reversed to refill the drug reservoir. This first configuration is most suited for a donut-type bellows to ensure that no contaminant reaches the interior of the drug reservoir.

In the second configuration of the second preferred embodiment of the present invention, a motor rotates a worm gear that displaces a rack coupled to the bottom portion of the drug reservoir. A flexible side bellows allows the drug reservoir base to be displaced upwards as the worm gear turns, forcing drug from the reservoir to the desired delivery site. Again, the motor may be programmed so that drug is delivered at a desired rate or pattern, and may be reversed to facilitate the refilling of the drug reservoir. The side bellows are hermetically sealed to keep the drug free of possible contamination from unwanted sources, and to protect any adverse impact which might result from their contacting the drugs.

The third embodiment of the present invention utilizes the spring force of the reservoir bellows to displace the drug reservoir. The bellows is annealed, so that in its relaxed, natural state it is completely collapsed. In this configuration (See FIG. 6), the bellows is expanded by a device such as a motor which turns a flywheel or pulley to wind one end of a cable about the pulley or flywheel, the other end of the cable being connected to the bottom of the drug reservoir. Once the reservoir is filled, the pulley/cable is relaxed to allow the bellows to return to its natural, collapsed state. Again, the motor may be programmed to any pattern or rate to ensure that the displaced drug is delivered according to the desired schedule, and the motor may be programmed to allow for controlled refilling.

As stated above, and although the present invention described herein in terms of three separate embodiments, there are certain advantages which all three embodiments share over prior devices. For example, again, in each embodiment the drug contacts only one material. Preferably, the material used is titanium or some other inert material suitable for use in a wide variety of medical applications. Moreover, the active mechanism in each embodiment, a pump or motor, is completely sealed off from the drug to be delivered. Further, there are no small passages for the drug to travel through, and the amount of dead space is minimized. Finally, the active mechanism is able to empty and refill the reservoir, eliminating the need for medical personnel to do so. This minimizes the possibility of overfilling.

DETAILED DESCRIPTION OF THE INVENTION

Figure 1:
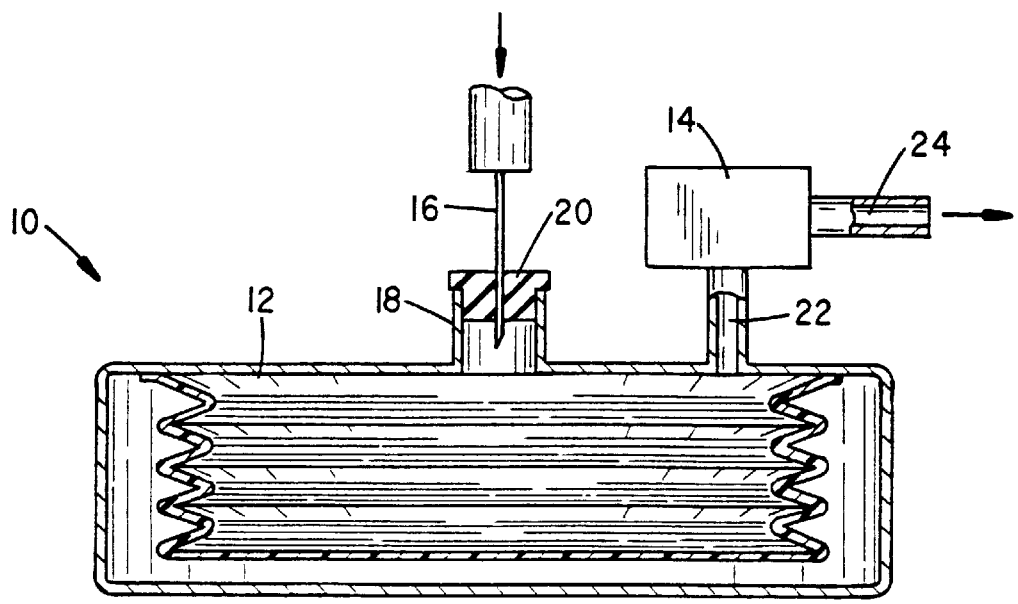
FIG. 1 is a schematic illustration of a conventional implantable drug infusion device.

As shown in FIG. 1, prior implantable drug infusion devices generally comprise an infusion assembly 10 including an internal drug reservoir 12 and a pump 14. A drug that is to be delivered to a specific desired location within a patient's body is supplied manually via a hypodermic needle 16 inserted into the reservoir 12. Access to the reservoir 12 is achieved through an access port 18 by inserting the needle 16 through the septum 20 which otherwise acts to prevent fluids or other substances from gaining entry to or leaving the reservoir 12. The pump 14 pulls the drug to be infused to the patient from reservoir 12 via exitway 22. After passing through pump 14, the drug is delivered via outlet line 24 to the desired location within the patient's body.

The use of prior implantable drug infusion devices such as the one shown generally in FIG. 1 has significant drawbacks. However, as noted above, the present invention overcomes these shortcomings. In particular, it should be noted that the drug in pump 10 contacts multiple different materials, that the pump 14 is in contact with the drug, that the drug must traverse any small passageway in pump 14, and that the rate of introduction of drug into reservoir 12 is controlled solely by the clinician filling the device and is not metered by pump 10.

Figure 2:
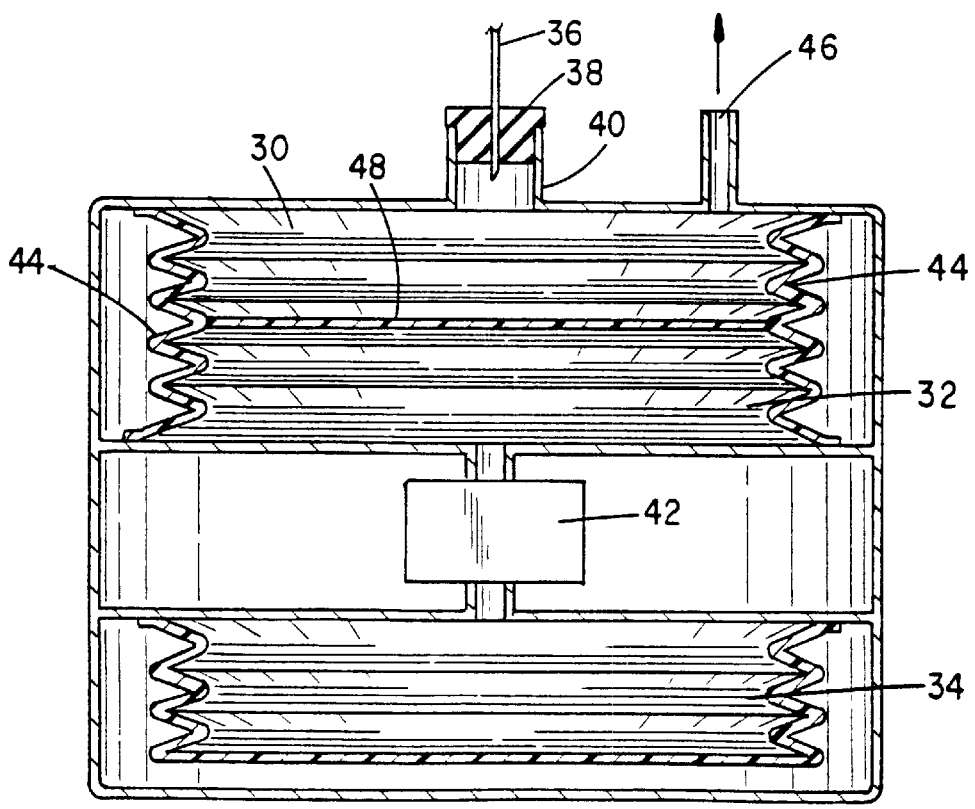
FIG. 2 is a schematic illustration of an embodiment of an implantable drug infusion device according to the present invention and including a diaphragm and a hydraulic displacement mechanism.

As shown in FIG. 2, the first configuration of what for convenience is termed herein as the "hydraulic" embodiment of the present invention includes three separate reservoirs: a first drug reservoir 30, a second intermediate reservoir 32, and a third lower reservoir 34. The drug to be infused to a desired location within a patient's body is introduced into reservoir 30 via needle 36 inserted through septum 38 disposed within access port 40.

In accordance with the present invention, intermediate chamber 32 initially contains a working fluid such as sterile water, sterile saline, silicone oil, or a lubricant. A membrane or diaphragm 48 separates drug reservoir 30 from intermediate reservoir 32. Once the delivery needle 36 is inserted in place so that its tip is within reservoir 30, the pump 42 draws working fluid from intermediate chamber 32 and delivers the withdrawn fluid into lower chamber 34. As the volume of fluid in intermediate chamber 32 decreases, the size of chamber 32 will decrease too, and drug fluid will be drawn into reservoir 30 from the supply needle 36. The change in volumes of reservoirs 30 and 32 is possible in view of the use of the bellows-like sidewall 44. The amount of working fluid transferred from intermediate chamber 32 to lower chamber 34 varies according to the desired amount of drug to be drawn into drug reservoir 30.

Once drug reservoir 30 holds a desired amount of drug fluid, and the needle 36 has been withdrawn, delivery of the drug to a specific desired location within a patient's body via outlet line 46 is accomplished by reversing pump 42. That is, pump 42 draws working fluid from lower chamber 34 and injects it into intermediate chamber 32. When this occurs, the volume of intermediate chamber 32 increases, and membrane 48 is displaced, so that the size of drug reservoir 30 decreases and drug is forced out through exitway 46.

Thus, by controlling the operation of pump 42, the delivery of drug to the patient is also controlled. Preferably, the pump 42 is programmable, allowing the physician or other clinician to set the rate and/or pattern of the transfer of the working fluid, and hence the rate and/or pattern for the infusion of drug fluid.

Figure 3:
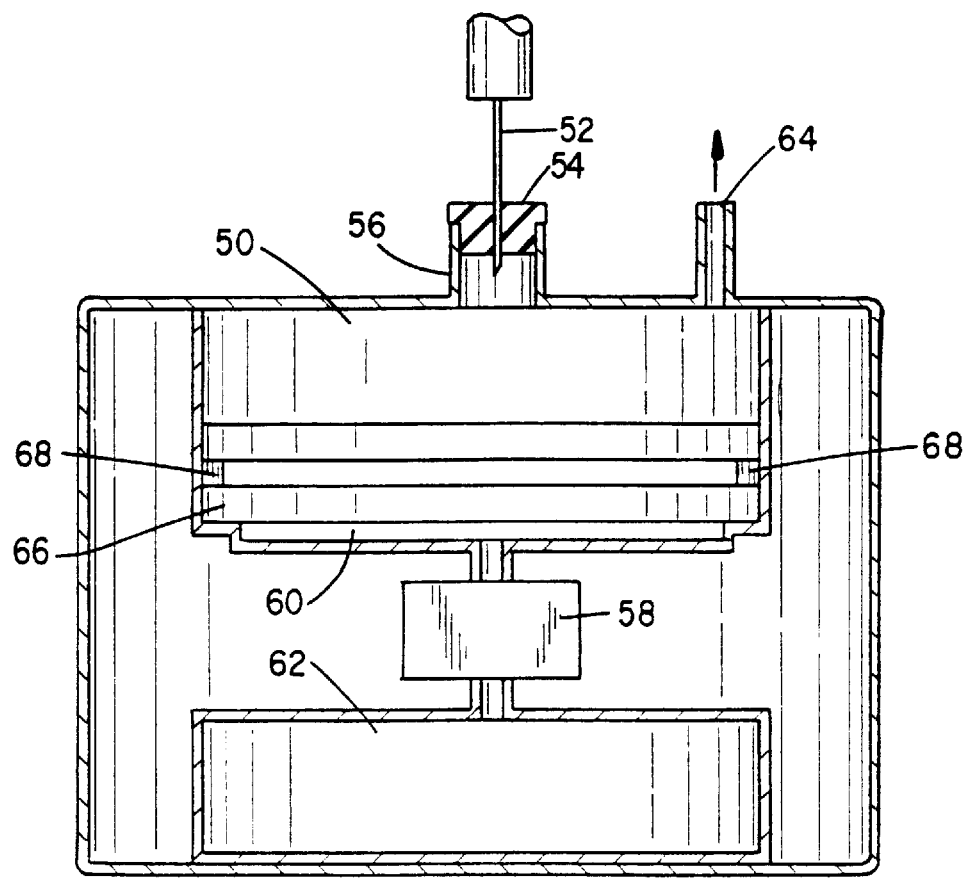
FIG. 3 is a schematic illustration of an embodiment of an implantable drug infusion device according to the present invention and including a piston and a hydraulic displacement method.

A second configuration of the "hydraulic" embodiment of the present invention is shown in FIG. 3. The structure of this second configuration generally resembles that of the first configuration. Drug is introduced into reservoir 50 via a needle 52 inserted through septum 54 disposed within access port 56. A pump 58 acts to transfer a working fluid between intermediate chamber 60 and a lower chamber 62. The drug is infused to the patient's body through exitway 64 by the action of pump 58, the transfer of the working fluid, and the displacement of the reservoir 50, much like the infusion takes place within the first configuration. However, the second hydraulic configuration includes, instead of a membrane, a sliding piston 66 adapted with a seal 68 to separate intermediate chamber 60 from drug reservoir 50. The seal 68 helps to ensure that no fluid or drug is transferred between chambers 50 and 60.

The second preferred embodiment of the present invention generally is directed to an assembly that uses mechanical, screw-type displacement of a drug reservoir to deliver pharmaceutical agents or other fluids to a specific desired locations within a patient's body. Again, there are two general configurations of this preferred embodiment.

Figure 4:
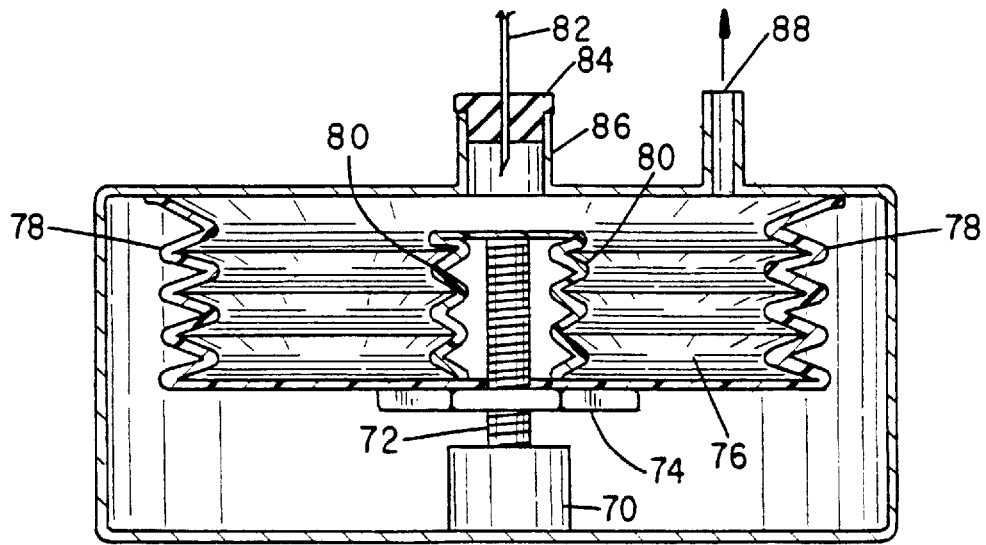
FIG. 4 is a schematic illustration of an embodiment of an implantable drug infusion device according to the present invention and incorporating direct mechanical displacement by a motor and lead screw.

In the first configuration, shown in FIG. 4, a motor 70 is operatively coupled to a lead screw 72, so that as the motor 70 rotates the screw 72, a nut 74 is displaced along the longitudinal axis of the screw 72. The nut 74 is operatively coupled to both lead screw 72 and the base of drug reservoir 76, so that displacement of the nut 74 in either direction along the axis of screw 72 results in a corresponding displacement of the base of the drug reservoir 76.

As the base of the drug reservoir 76 moves, the volume of the drug chamber 76 changes. Preferably, sidewall 78 and inner wall 80 comprise a donut-shaped bellows-like assembly that permits the volume change to occur.

The introduction and expulsion of the drug to and from the drug reservoir 76 is accomplished much like in the first preferred embodiment of the present invention, i.e., by displacement of the drug reservoir itself. Again, access to the reservoir 76 may be had by way of a needle 82 inserted through a septum 84 disposed within access port 86, and the drug exits the reservoir 76 via exitway 88.

Figure 5:
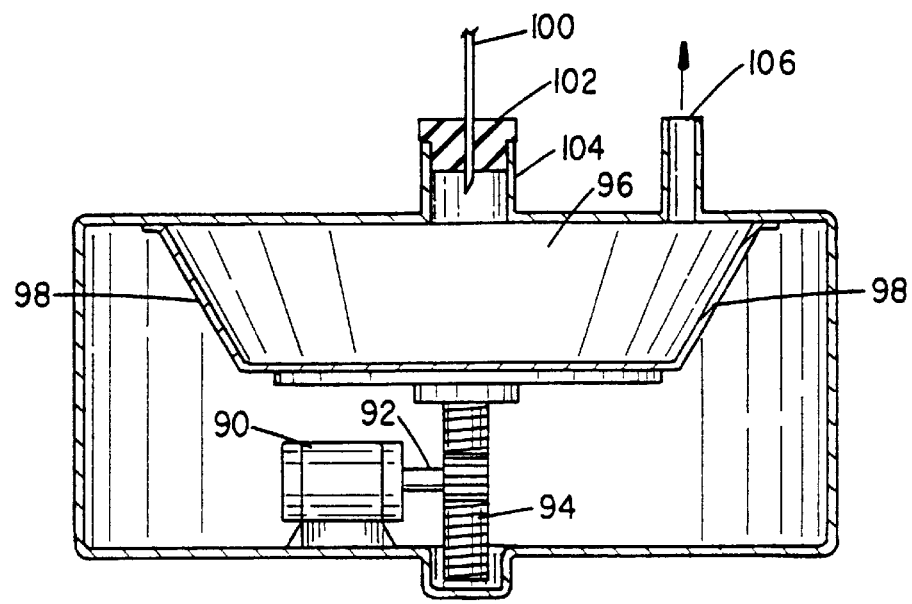
FIG. 5 is a schematic illustration of an embodiment of an implantable drug infusion device according to the present invention and incorporating direct mechanical displacement by a worm gear.

The second configuration of the second preferred embodiment is shown in FIG. 5. A motor 90 drives a worm gear 92 that meshes with a toothed bar or rack 94. The rack 94 is fixedly attached or otherwise operatively coupled on one end to the bottom of the drug reservoir 96. The drug reservoir 96 is shown as having flexible, i.e., collapsible sides 98, rather than bellows-like sides as in the other Figures. The exact shape of the sides is not necessarily critical; of primary importance is that the sides allow the reservoir 96 to be displaced, so that drug introduced by needle 100 through septum 102 disposed in port 104 may be delivered via exitway 106 to a specific desired location in the patient's body.

Figure 6:
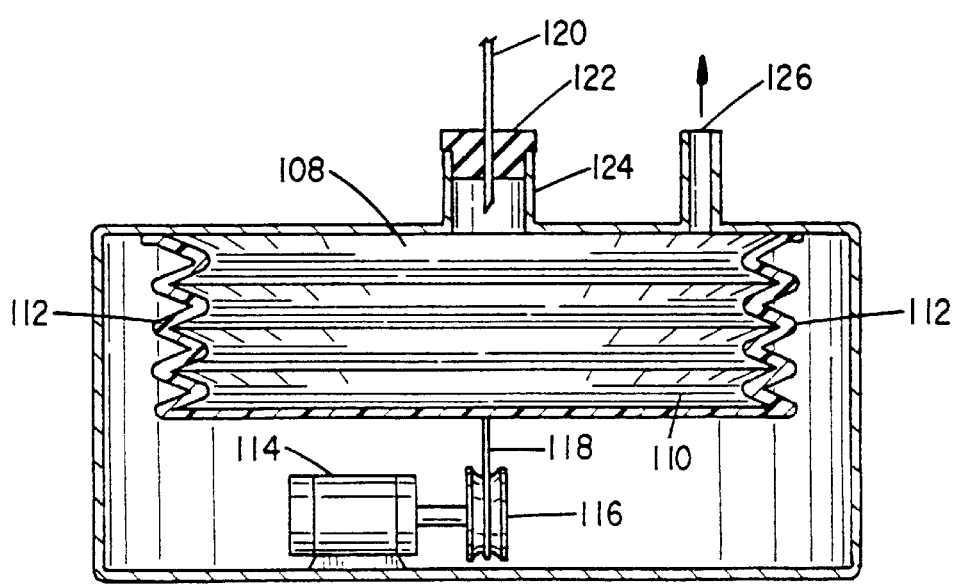
FIG. 6 is a schematic illustration of an embodiment of an implantable drug infusion device according to the present invention and incorporating a spring forced bellows urgeable from a relaxed collapsed position by a pulley mechanism.

The third preferred embodiment of the present invention is shown in FIG. 6. The drug infusion assembly comprises a reservoir 108 including a base 110 and bellows 112. The bellows 112 preferably is annealed in a bellows-like shape so that in its natural state the wall is collapsed, i.e., in a condition corresponding to the state of lowest volume of the reservoir 108. A motor 114 is operatively coupled to a pulley or flywheel 116. A wire, rope, cord, chain or similar such connecting means 118 is coupled on one end to the base 110, and on its other end to the flywheel 116. As the motor 114 turns in one direction, the flywheel 116 turns and wraps the connecting means 118 about the flywheel 116, so that the base 110 is displaced, increasing the volume of the reservoir 108. As the volume of the reservoir 108 is increased, drug or other fluids to be infused to the patient may be introduced into the reservoir 108 from the needle 120 extending through septum 122 disposed in port 124 in the manner described above. The annealing of the bellows 112 ensures that the reservoir acts like a spring; that is, in tending toward a natural state, the reservoir places in tension the connecting means 118.

To deliver drug to the patient, then, the direction of the motor 114 is reversed, so that the reservoir is displaced back toward its natural state. As the volume of the reservoir decreases, the drug is forced to exit through opening 126. The motor 114, like the motors and pumps of the other embodiments, may be programmed so that delivery of the drug takes place at a desired rate or pattern.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A method of infusing a drug to a specific desired location within a patient's body, comprising:

implanting a first reservoir, a second reservoir situated directly adjacent the first reservoir, a third reservoir in fluid communication with the second reservoir, and a pump operatively connected between the second and third reservoirs within the patient's body, the second reservoir containing a working fluid;

providing a supply of the drug in fluid communication with the first reservoir;

operating the pump to transfer working fluid from the second reservoir to the third reservoir to increase the volume of the first reservoir and draw at least a portion of the provided supply of the drug into the first reservoir; and operating the pump to transfer working fluid from the third reservoir to the second reservoir to decrease the volume of the first reservoir and deliver at least a portion of the drug from the first reservoir and through an established fluid passageway extending between the first reservoir and the specific desired location within the patient's body.

2. A method of drawing a drug fluid into a drug infusion device implanted in the body, comprising:

implanting a first reservoir, a second reservoir situated directly adjacent the first fluid reservoir, a third reservoir in fluid communication with the second reservoir, and a pump operatively connected between the second and third reservoirs within the body, the second reservoir containing a working fluid;

providing a supply of the drug fluid in fluid communication with the first reservoir of the infusion device; and operating the pump to transfer working fluid from the second reservoir to the third reservoir thus increasing the volume of the first reservoir to draw the drug fluid into the first reservoir.

3. The method of claim 2, wherein providing the supply of the drug fluid includes inserting a delivery needle into the first reservoir.

4. The method of claim 2, wherein the first reservoir includes a bellows, and wherein operating the pump to transfer working fluid from the second reservoir to the third reservoir includes pumping the working fluid from the second reservoir to the third reservoir to expand the bellows, thus increasing the volume of the first reservoir.

5. The method of claim 2, wherein the drug infusion device includes a sliding piston situated between the first reservoir and the second reservoir, and wherein operating the pump to transfer working fluid from the second reservoir to the third reservoir includes pumping the working fluid from the second reservoir to the third reservoir to move the sliding piston in a first direction, thus increasing the volume of the first reservoir.

6. A method of infusing a drug fluid into a body from a drug infusion device implanted in the body, the method comprising:

implanting a first reservoir, a second reservoir situated directly adjacent the first fluid reservoir, a third reservoir in fluid communication with the second reservoir, and a pump operatively connected between the second and third reservoirs within the body, the third reservoir containing a working fluid;

providing a supply of the drug fluid into the first reservoir; and operating the pump to transfer working fluid from the third reservoir to the second reservoir to reduce the volume of the first reservoir thus delivering the drug fluid from the first reservoir to the body.

7. The method of claim 6, wherein the first reservoir includes a bellows, and wherein operating the pump to transfer the working fluid includes pumping the working fluid from the third reservoir to the second reservoir to collapse the bellows, thus reducing the volume of the first reservoir.

8. The method of claim 7, further comprising:

providing the supply of the drug fluid external to the body in fluid communication with the first reservoir; and operating the pump to transfer working fluid from the second reservoir to the third reservoir to expand the bellows, thus increasing the volume of the first reservoir to draw the drug fluid into the first reservoir.

9. The method of claim 6, wherein the drug infusion device includes a sliding piston situated between the first reservoir and the second reservoir, and wherein operating the pump to transfer the working fluid includes pumping the working fluid from the third reservoir to the second reservoir to move the sliding piston in a first direction, thus reducing the volume of the first reservoir.

10. The method of claim 9, further comprising:

providing the supply of the drug fluid external to the body in fluid communication with the first reservoir; and operating the pump to transfer working fluid from the second reservoir to the third reservoir to move the sliding piston in a second direction, thus increasing the volume of the first reservoir to draw the drug fluid into the first reservoir.

* * * * *